(12) United States Patent
Dominguez et al.

(10) Patent No.: US 10,556,081 B2
(45) Date of Patent: Feb. 11, 2020

(54) BRAIDED HOSE FOR USE IN SLEEP APNEA TREATMENT SYSTEMS THAT DECOUPLES FORCE

(71) Applicant: Fresca Medical Inc., San Clemente, CA (US)

(72) Inventors: Andrew Dominguez, San Clemente, CA (US); Richard Ewers, Fulterton, CA (US)

(73) Assignee: FRESCA MEDICAL, INC., San Clemente, CA (US)

( * ) Notice: Subject to any disclaimer, the term of this patent is extended or adjusted under 35 U.S.C. 154(b) by 0 days.

(21) Appl. No.: 16/378,780

(22) Filed: Apr. 9, 2019

(65) Prior Publication Data

US 2019/0232011 A1 Aug. 1, 2019

Related U.S. Application Data

(60) Division of application No. 16/133,665, filed on Sep. 17, 2018, now Pat. No. 10,315,000, which is a
(Continued)

(51) Int. Cl.

| | |
|---|---|
| *F16L 11/02* | (2006.01) |
| *A61M 16/06* | (2006.01) |
| *A61M 16/00* | (2006.01) |
| *F16L 11/04* | (2006.01) |
| *F16L 11/10* | (2006.01) |

(Continued)

(52) U.S. Cl.
CPC .... *A61M 16/0666* (2013.01); *A61M 16/0003* (2014.02); *A61M 16/0816* (2013.01); *F16L 11/02* (2013.01); *F16L 11/04* (2013.01); *F16L 11/10* (2013.01); *A61B 5/4818* (2013.01); *A61F 5/566* (2013.01); *A61M 16/06* (2013.01); *A61M 2205/0216* (2013.01); *A61M 2205/0266* (2013.01)

(58) Field of Classification Search
CPC .. F16L 11/02; F16L 11/04; F16L 11/10; F16L 11/24
USPC ......................................................... 138/126
See application file for complete search history.

(56) References Cited

U.S. PATENT DOCUMENTS

| | | |
|---|---|---|
| 3,586,058 A | 6/1971 | Ahrens |
| 4,332,278 A | 6/1982 | Lalikos |
| | (Continued) | |

OTHER PUBLICATIONS

ISR for PCT/US2018/051399 dated Jan. 16, 2019.

*Primary Examiner* — Craig M Schneider
*Assistant Examiner* — David R Deal
(74) *Attorney, Agent, or Firm* — Manuel de la Cerra

(57) ABSTRACT

A hose is described that includes a braided matrix with an interior lumen. The matrix also includes filaments that intersect each other and create a braid, and a longitudinal axis that runs along the lumen, wherein the filaments intersect the longitudinal axis at a braid angle. The braid angle can be varied by compressing or expanding the matrix along the direction of the longitudinal axis. A polymer coating is applied to the matrix such that the matrix is substantially impermeable to air. The hose has two states: (1) a relaxed state, where the hose does not experience a force in the direction of the longitudinal axis; and (2) a stressed state where the hose experiences a force in the direction of the longitudinal axis. The braid angle is larger in the relaxed state as compared to the stressed state. A method of manufacture for the hose is also disclosed.

5 Claims, 14 Drawing Sheets

Related U.S. Application Data continuation-in-part of application No. 15/557,907, filed as application No. PCT/US2016/023798 on Mar. 23, 2016.

(60) Provisional application No. 62/722,580, filed on Aug. 24, 2018, provisional application No. 62/694,126, filed on Jul. 5, 2018, provisional application No. 62/686,442, filed on Jun. 18, 2018, provisional application No. 62/246,477, filed on Oct. 26, 2015.

(51) Int. Cl.
*A61M 16/08* (2006.01)
*A61F 5/56* (2006.01)
*A61B 5/00* (2006.01)

(56) References Cited

U.S. PATENT DOCUMENTS

| | | |
|---|---|---|
| 4,420,018 A | 12/1983 | Brown |
| 4,452,279 A | 6/1984 | Atwell |
| 8,752,591 B2 | 6/2014 | Montalvo |
| 9,046,201 B1 | 6/2015 | Theis |
| 2007/0251593 A1 | 11/2007 | Noda |
| 2008/0236695 A1 | 10/2008 | Takagi |
| 2009/0205736 A1 | 8/2009 | Mezzalira |
| 2009/0236004 A1 | 9/2009 | Jani |
| 2010/0236655 A1 | 9/2010 | Gregrich |
| 2012/0090720 A1 | 4/2012 | Burrowes |
| 2014/0220276 A1 | 8/2014 | Gao |
| 2014/0246025 A1 | 9/2014 | Fresca |
| 2015/0330538 A1 | 11/2015 | Clark |
| 2015/0354731 A1 | 12/2015 | Ragner |
| 2017/0137978 A1 | 5/2017 | Gao et al. |
| 2017/0226671 A1 | 8/2017 | Zhang et al. |

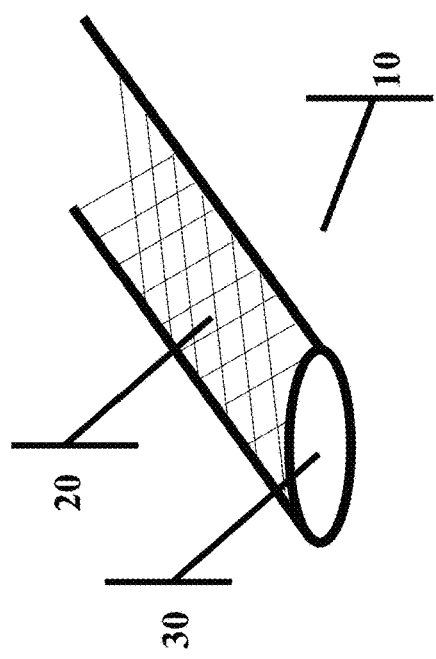
FIG. 5
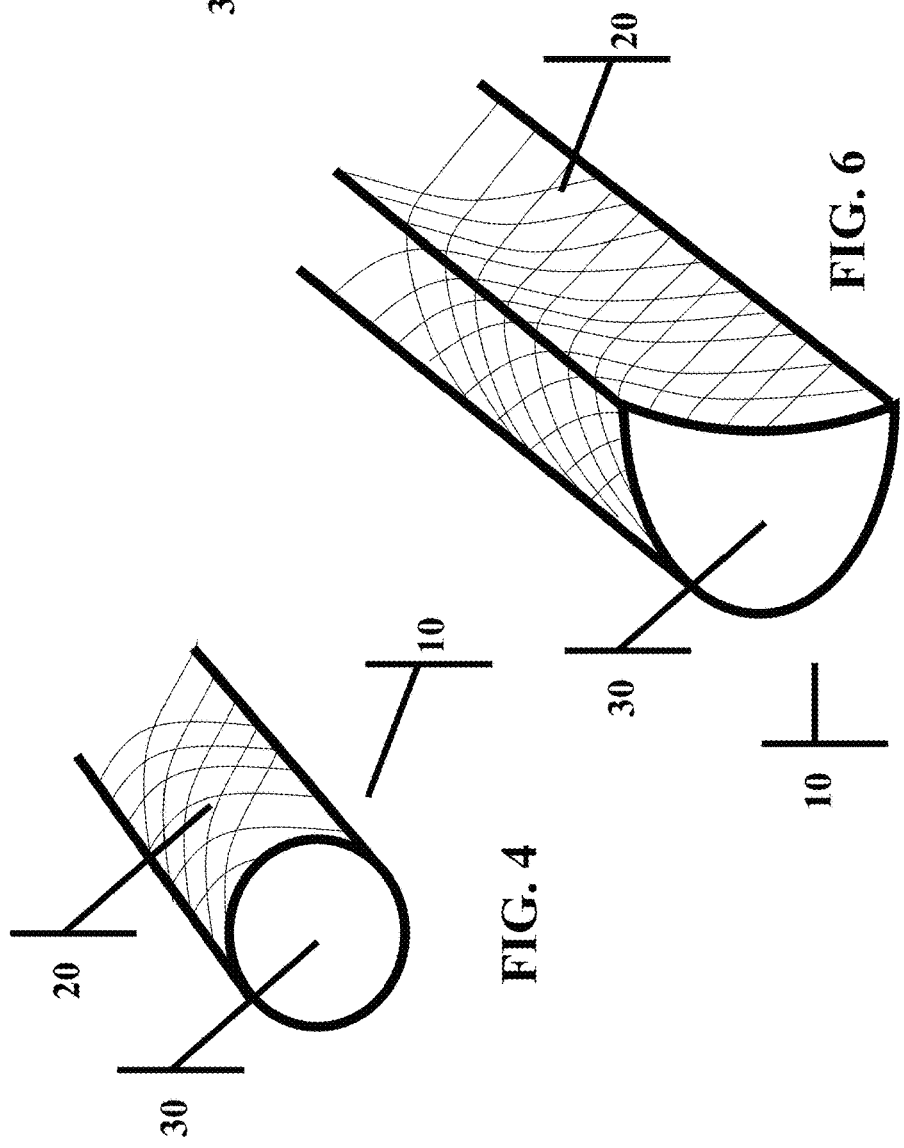
FIG. 6
FIG. 4

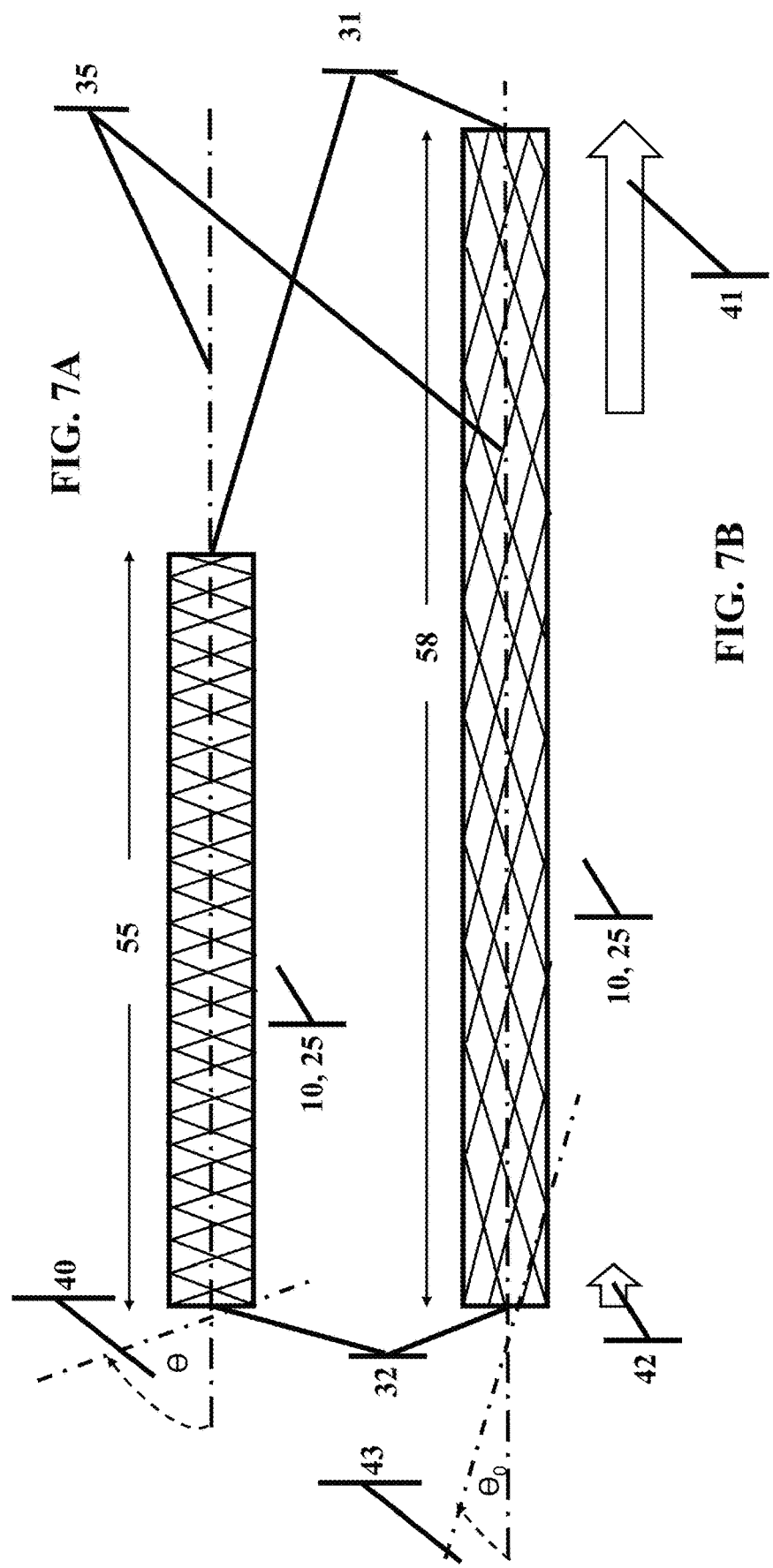

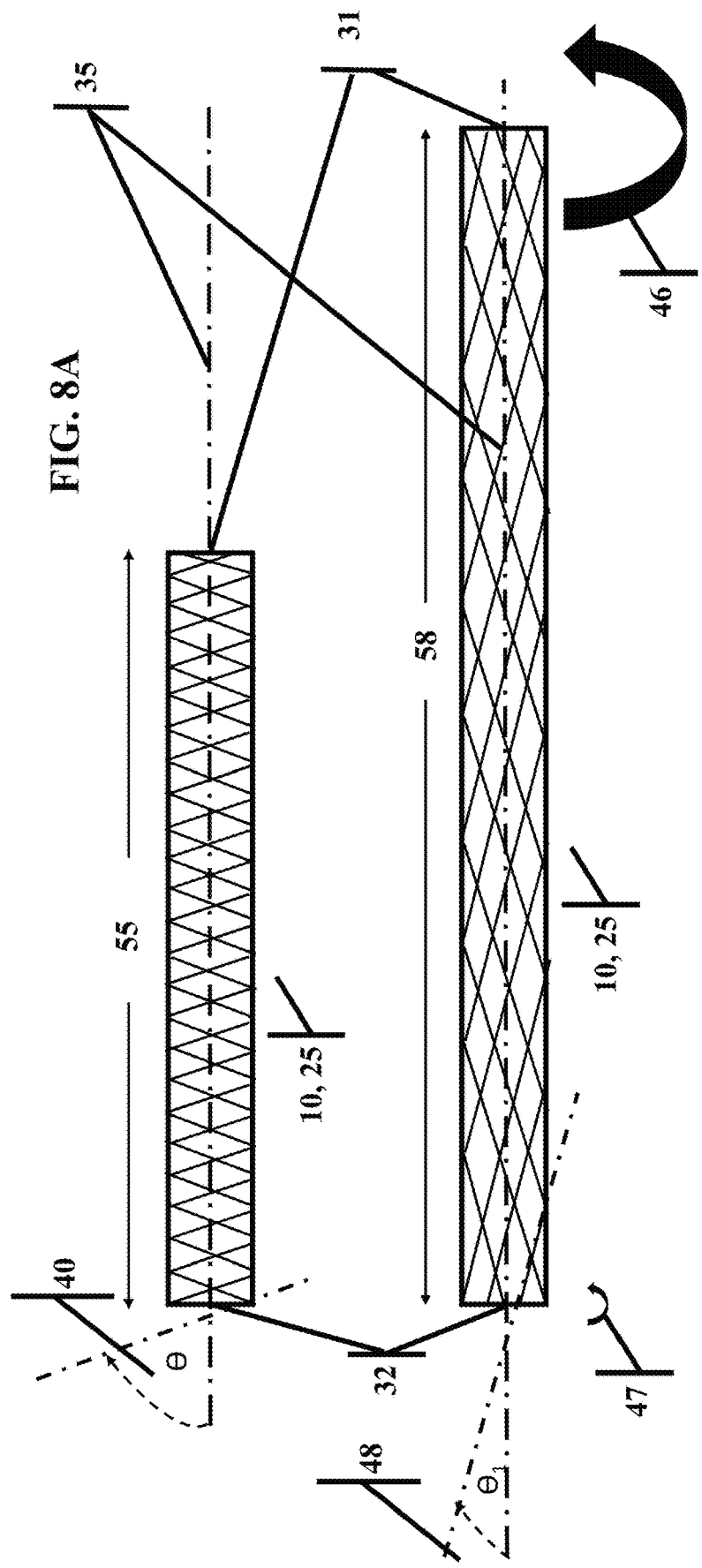

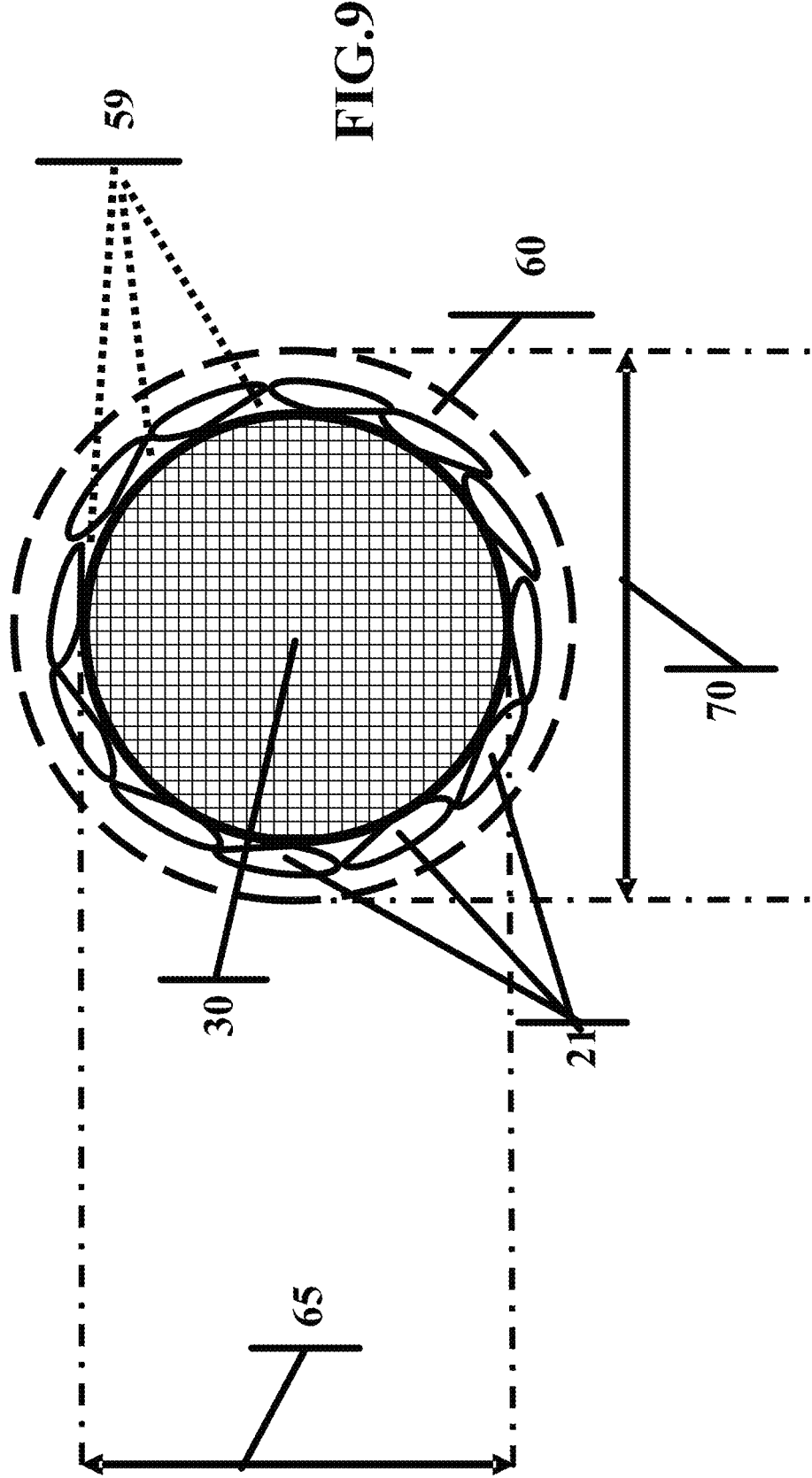

BRAIDED HOSE FOR USE IN SLEEP APNEA TREATMENT SYSTEMS THAT DECOUPLES FORCE

RELATED APPLICATIONS

The assignee of this application, FRESCA Medical, has described various embodiments of its valved Positive Airway Pressure (PAP) sleep apnea treatment mask. Those embodiments are described in U.S. patent application Ser. No. 13/860,926, filed Apr. 11, 2013, titled "Sleep Apnea Device," U.S. Provisional Application Ser. No. 61/623,855, filed Apr. 13, 2012, titled "Sleep Apnea Device," U.S. Provisional Application Ser. No. 61/775,430, filed Mar. 8, 2013, titled "Sleep Apnea Device," U.S. Provisional Application No. 61/823,553, filed May 15, 2013, titled "Sleep Apnea Device," U.S. Provisional Application No. 61/838,191, filed Jun. 21, 2013, titled "Sleep Apnea Device," U.S. Provisional Application No. 61/962,501, filed Nov. 8, 2013, titled "Sleep Apnea Device," U.S. Provisional Application No. 61/909,956, filed Nov. 27, 2013, titled "Sleep Apnea Device," U.S. Provisional Application No. 61/927,355, filed Jan. 14, 2014, titled "Valve with Pressure Feedback," U.S. Provisional Application No. 62/134,506 filed Mar. 17, 2015 titled "Valve with Pressure Feedback Draft Provisional Application," U.S. Provisional Application No. 62/163,601, filed May 19, 2015, titled "Airflow Generator with Delayed Onset", U.S. Provisional Application No. 62/184,787, filed Jun. 25, 2015, titled "Sleep Apnea Device," U.S. Provisional Application No. 62/239,146, filed Oct. 8, 2015, titled "Sleep Apnea Device," U.S. patent application Ser. No. 14/930,284, filed Nov. 2, 2015, titled "Apparatus, System and Methods for Treating Obstructive Sleep Apnea", U.S. Provisional Application No. 62/246,339 filed Oct. 26, 2015 titled "Venting of a Valved CPAP Mask to Create a Comfortable Breathing Sensation," U.S. Provisional Application No. 62/246,489 filed Oct. 26, 2015, titled "Managing Sleep Apnea with Pulse Oximeters and With Additional Assessment Tools," U.S. Provisional Application No. 62/246,328, filed Oct. 26, 2015, titled "Novel Low Flow Technology Designed to Meet CPAP Efficacy," U.S. Provisional Application No. 62/246,477, filed Oct. 26, 2015, titled "Composite Construction Air Delivery Hose for Use with CPAP Treatment," U.S. Provisional Application No. 62/275,899, filed Jan. 7, 2016, titled "Valved Mask To Reduce and Prevent Snoring," U.S. Provisional Application No. 62/311804, filed Mar. 22, 2016, titled "Improvements to Sleep Apnea Machine," U.S. Provisional Application No. 62/382,980, filed Sep. 2, 2016, titled "Dual Rotatable Hose For Use With CPAP Treatment," U.S. application Ser. No. 15/334,243, filed Oct. 15, 2016, titled "Apparatus, Systems, and Methods For Treating Obstructive Sleep Apnea," U.S. Provisional Application No. 62/532,240, filed July 13, 2017, titled "Sleep Apnea Treatment System and Improvements Thereto," U.S. Provisional Application No. 62/595,529, filed Dec. 6, 2017, titled "Sleep Apnea Treatment System and Improvements Thereto," U.S. patent application Ser. No. 15/557,907, filed on Sep. 13, 2017, titled "Apparatus, Systems, and Methods For Treating Obstructive Sleep Apnea," U.S. Provisional Application No. 62/465,905, filed Mar. 2, 2017, titled "Sound Mitigation/Flow Optimization in a Valved Obstructive Sleep Apnea Treatment Mask," U.S. patent application Ser. No. 16/034,980, filed on Jul. 13, 2018, titled "Sleep Apnea Treatment System and Improvements Thereto," and U.S. patent application Ser. No. 16/034,967, filed on Jul. 13, 2018, titled "Sleep Apnea Treatment System and Improvements Thereto," all of which are hereby incorporated by reference in their entirety. Disclosed in this document are particular features and structures that may be used in conjunction with the previously disclosed embodiments.

This application further claims priority as the non-provisional of U.S. Provisional Application No. 62/722,580, filed on Aug. 24, 2018, titled "Braided Hose For Use in Sleep Apnea Treatment Systems that Decouples Forces," claims priority as the non-provisional U.S. Provisional Application No. 62/686,442, filed on Jun. 18, 2018, titled "Braided Hose For Use in Sleep Apnea Treatment Systems that Decouples Forces," claims priority as the non-provisional of U.S. Provisional Application No. 62/694,126, filed on Jul. 5, 2018, titled "Braided Hose For Use in Sleep Apnea Treatment Systems that Decouples Forces," and also claims priority as a divisional of U.S. application Ser. No. 16/133,665, filed on Aug. 24, 2018, titled "Braided Hose For Use in Sleep Apnea Treatment Systems that Decouples Forces," which in turn claims priority as a continuation-in-part of U.S. patent application Ser. No. 15/557,907, filed on Sep. 13, 2017, titled "Apparatus, Systems, and Methods For Treating Obstructive Sleep Apnea," which in turn claims priority to PCT/US16/23798 titled "Apparatus, Systems, and Methods For Treating Obstructive Sleep Apnea," filed on Mar. 23, 2016, which in turn claims priority to U.S. Provisional Application No. 62/246,477, filed on Oct. 26, 2015, titled "Composite Construction Air Delivery Hose for Use with CPAP Treatment"; the entire contents of each of these applications is hereby incorporated by reference.

TECHNICAL FIELD

The present invention is related to medical systems, devices, and methods. More specifically, the invention is related to systems, devices and methods for treating obstructive sleep apnea or snoring.

BACKGROUND

Most Positive Airway Pressure (PAP) systems require some form of tube, hose, or conduit for the delivery of breathable gas. This gas is used for the pressurization, 2-30 cm $H_2O$, of the upper airway for the treatment of disordered breathing, typically obstructive sleep apnea (OSA). Hoses connect at one end to the flow generator and connect at the other end to the user via a full face, nasal or nasal pillows mask. Current hose embodiments are uncomfortable, heavy, and cumbersome and are susceptible to unintentional disconnection of the hose from the flow generator and/or mask. In some cases, current hose designs can even result in the user pulling the flow generator off of a nearby nightstand or side table, causing damage to the device. These problems are a result of the current hose embodiments' size, weight, inflexibility, propensity to become entangled with the user or the bedding material, and inability to stretch. Due to the problems inherent in the design of current PAP hoses, a wide range of devices has been developed to help alleviate these problems without addressing the inherent design of the hose itself, such as specialty pillows, hose clips, or hose suspension systems.

The main problem with current hose embodiments is that they do not attenuate the forces enacted upon them. The result of this lack of attenuation is the transmission of forces from the hose to the mask and/or to the flow generator. These forces can cause anything from minor leaks to disconnection. A minor leak will reduce the effectiveness of the therapy and may disturb the user's sleep. The greater the leak, the more negative the impact will be on the efficacy of treatment. During the night, users will often wrestle, struggle with, get caught in, and/or get wrapped around their hose, thereby pulling or tugging on it. These forces will be transmitted to the mask and/or flow generator and may cause leaks, or cause the flow generator to fall to the floor, without some sort of attenuation. In either case, the patient's therapy is diminished or interrupted, as is the patient's sleep. Typical PAP hoses are six feet in length, which is in most cases at least double the distance between the flow generator and the user. Current hoses rely on the slack in the length of the hose to mitigate forces applied to them by the user or by the bedding. If the hose becomes anchored or pinned along its length by the user, or on some part of the bed, the additional length can no longer be used for force mitigation. While anchored, only the remaining functional length of the hose, that length between the anchor point and the flow generator or mask, can utilize its slack to attenuate the forces enacted upon it. Without the full length of the hose, the ability of the slack of the hose to mitigate the forces acting upon the hose can be greatly diminished and movement from the user may cause partial to full disconnection from the flow generator and/or the mask.

Therefore, a need exists for a lightweight hose that can attenuate the forces so that the therapy and the quality of sleep is not impaired while using a PAP system.

SUMMARY

A hose is described that includes a braided matrix with an interior lumen. The matrix includes filaments that intersect each other, creating a braid. A longitudinal axis runs along the lumen, and the filaments intersect the longitudinal axis at a braid angle. The braid angle can be varied by compressing or expanding the matrix along the direction of the longitudinal axis. A polymer coating is applied to the matrix such that the matrix is substantially impermeable to air. The hose has two states: (1) a relaxed state, where the hose does not experience a force in the direction of the longitudinal axis; and (2) a stressed state, where the hose experiences a force in the direction of the longitudinal axis. The braid angle is larger in the relaxed state as compared to the stressed state.

The hose may have a first end and a second end, wherein the first end experiences a force in the direction of the longitudinal axis, and the hose attenuates the force as experienced by the second end. The attenuation of the force from the first end to the second end is proportional to the distance the first end has traveled away from the second end.

The hose may also have two additional states: (1) a rotationally relaxed state, where the hose does not experience a rotational force about the longitudinal axis; and (2) a rotationally stressed state, where the hose experiences a rotational force about the longitudinal axis. The braid angle differs between the rotationally relaxed state and the rotationally stressed state. The hose may further attenuate the rotational force as experienced by an end of the hose.

The braid angle may be at least 30 degrees larger in the relaxed state as compared to the stressed state, and the hose can be stretched to at least 130% of its length. The hose may have an outer diameter ranging from 0.3 to 0.5 in.

The filaments have a diameter ranging from 0.005-0.015 in and may have a cross-sectional shape selected from a group consisting of round, flat, or combinations of both. The filament may be comprised of a heat-shapeable material selected from a group consisting of: Nylon, PET, PEN, PP, PEEK, or a shape-memory metal. Non-heat-shapeable filaments, such as conductive element filaments, may be added in conjunction with the previously listed materials to the braided matrix.

The polymer coating may be less than 0.03 in and may be made of a silicone dispersion.

The braid may have a braid pattern that includes a first set of filaments that travels under a second set of filaments, and then travels over a third set of filaments, where the first set of filaments travels in a first rotation about the longitudinal axis and the second set of filaments travels in a second rotation about the longitudinal axis, wherein the first rotation of the first set is opposite to the second rotation of the second set.

The hose may have a bend radius of 0.7 in without the hose kinking.

A method of manufacture for the hose is also disclosed.

Additional aspects, alternatives and variations as would be apparent to persons of skill in the art are also disclosed herein and are specifically contemplated as included as part of the invention. The invention is set forth only in the claims as allowed by the patent office in this or related applications, and the following summary descriptions of certain examples are not in any way to limit, define or otherwise establish the scope of legal protection.

BRIEF DESCRIPTION OF DRAWINGS

The invention can be better understood with reference to the following figures. The components within the figures are not necessarily to scale, emphasis instead being placed on clearly illustrating example aspects of the invention. In the figures, like reference numerals designate corresponding parts throughout the different views and/or embodiments. Furthermore, various features of different disclosed embodiments can be combined to form additional embodiments, which are part of this disclosure. It will be understood that certain components and details may not appear in the figures to assist in more clearly describing the invention.

FIG. 4 shows a cross-sectional area of a round hose, including the interior lumen of the hose.

FIG. 5 shows a cross-sectional area of a flat-shaped hose.

FIG. 6 shows a hose whose cross-sectional area is a combination of round and flat shapes.

FIG. 7A represents the braided hose and shows the corresponding braid angle in a longitudinally relaxed state.

FIG. 7B represents the braided hose and shows the corresponding braid angle in a longitudinally stressed state.

FIG. 8A illustrates the braided hose and shows the corresponding braid angle in a rotationally relaxed state.

FIG. 8B illustrates the braided hose and shows the corresponding braid angle in a rotationally stressed state.

FIG. 9 is a not-to-scale schematic illustrating the coating of polymer on the braided matrix from a cross-sectional view.

DETAILED DESCRIPTION

Figure 1:
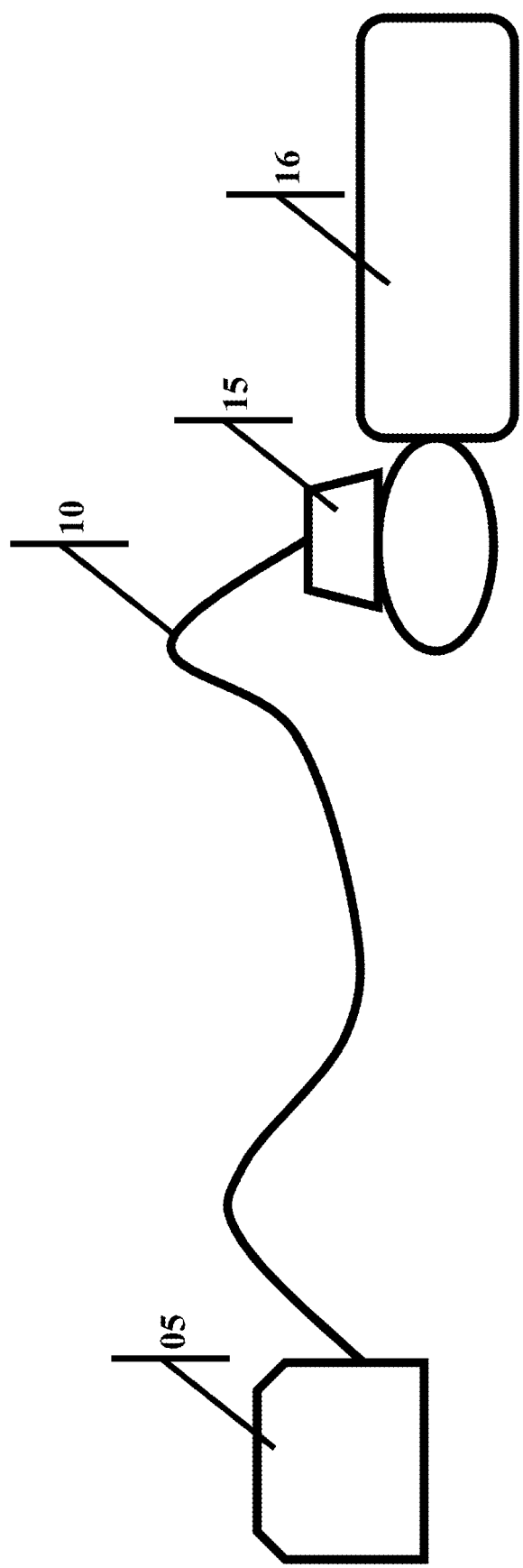
FIG. 1 shows a schematic of a hose connected to a PAP machine (flow generator) and a sleep mask, as one possible application of the present invention.

Reference is made herein to some specific examples of the present invention, including any best modes contemplated by the inventor for carrying out the invention. Examples of these specific embodiments are illustrated in the accompanying figures. While the invention is described in conjunction with these specific embodiments, it will be understood that it is not intended to limit the invention to the described or illustrated embodiments. To the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, process operations well known to persons of skill in the art have not been described in detail in order not to obscure unnecessarily the present invention. Various techniques and mechanisms of the present invention will sometimes be described in singular form for clarity. However, it should be noted that some embodiments include multiple iterations of a technique or multiple mechanisms, unless noted otherwise. Similarly, various steps of the methods shown and described herein are not necessarily performed in the order indicated, or performed at all in certain embodiments. Accordingly, some implementations of the methods discussed herein may include more or fewer steps than those shown or described. Further, the techniques and mechanisms of the present invention will sometimes describe a connection, relationship or communication between two or more entities. It should be noted that a connection or relationship between entities does not necessarily mean a direct, unimpeded connection, as a variety of other entities or processes may reside or occur between any two entities. Consequently, an indicated connection does not necessarily mean a direct, unimpeded connection unless otherwise noted.

The following list of example features corresponds to FIGS. 1-11 and is provided for ease of reference, where like reference numerals designate corresponding features throughout the specification and figures:

PAP blower/flow generator 05
Hose or tube with braided matrix and interior lumen (braided hose/tube) 10
  Sleep mask 15
  Person or user of PAP system 16
  Braided matrix 20
  Monofilament(s) 21
  Braiding pattern 25
  First set of filaments 26
  Direction of the rotation of the first set of filaments about the hose 26A
  Second set of filaments 27
  Direction of the rotation of the second set of filaments about the hose 27A
  Third set of filaments 28
  Interior lumen 30
  First end of the braided hose 31
  Second end of the braided hose 32
  Longitudinal axis 35
  Relaxed state braid angle θ 40
  Longitudinal force at the first end of the braided hose 41
  Longitudinal force at the second end of the braided hose 42
  Longitudinally stressed state braid angle $θ_a$ 43
  Rotational force at the first end of the braided hose 46
  Rotational force at the second end of the braided hose 47
  Rotationally stressed state braid angle 48
  Braided matrix relaxed state length l 50
  Braided matrix relaxed state width W 51
  Braided matrix longitudinally stressed state length $l_0$ 53
  Braided matrix longitudinally stressed state width $W_0$ 54
  Braided hose relaxed state length 55
  Braided hose longitudinally stressed state length 58
  Interstitial spaces of the braided matrix 59
  Polymer coating 60
  Inner diameter of the finished braided hose 65
  Outer diameter of the finished braided hose 70
  Braided hose bend radius 75
Method of manufacturing a braided hose 100
  Step of providing a braided matrix with an interior lumen 105
  Step of compressing the braided matrix 115
  Step of stabilizing the braid angle 125
  Step of applying a polymer to the matrix 135
Heat set braided matrix 200
  Heater ring 205
  Stationary mandrel 210
  Mobile mandrel 212
  Movement of mobile mandrel 213
  Spool track with monofilament carriers 215
  Spool plane 220
  Convergence zone 225
  Shielded or insulated metal wires, open lumens, or heatable elements 230

Figure 2A:
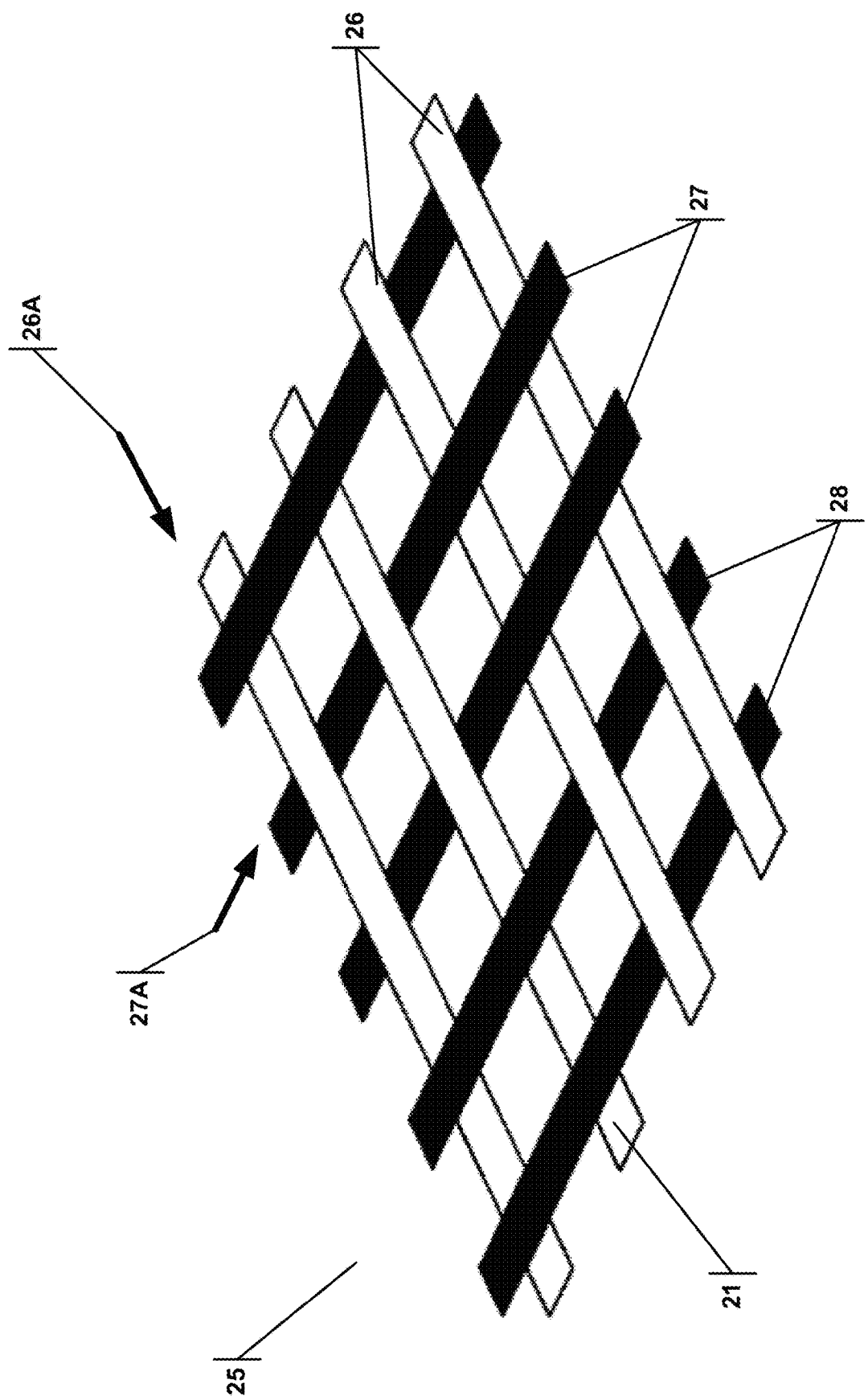
FIG. 2A illustrates a 2-dimensional rendition of a single-ended braiding pattern that may be used for the braided matrix of the hose.
Figure 2B:
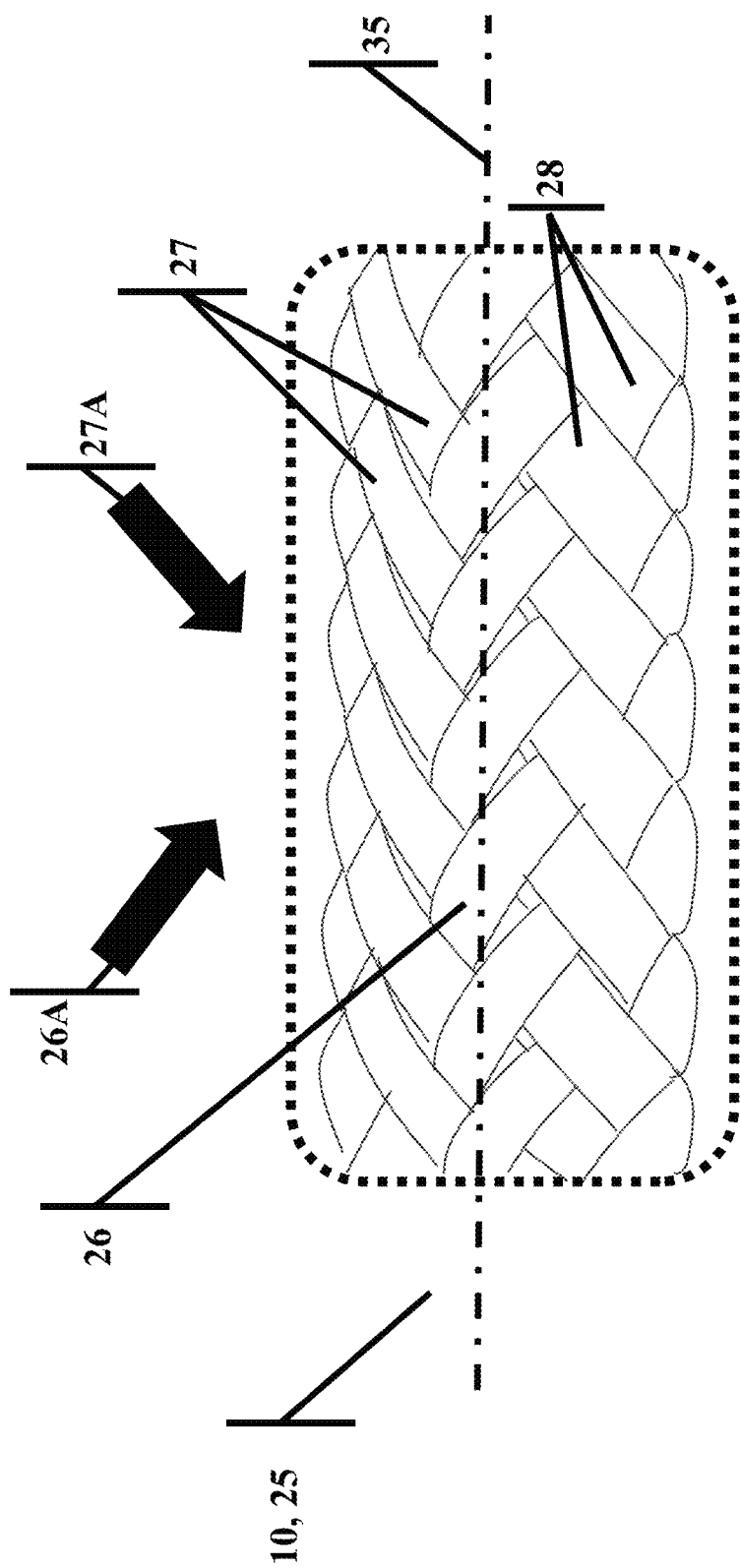
FIG. 2B shows an embodiment of the braided matrix on the hose.
Figure 2C:
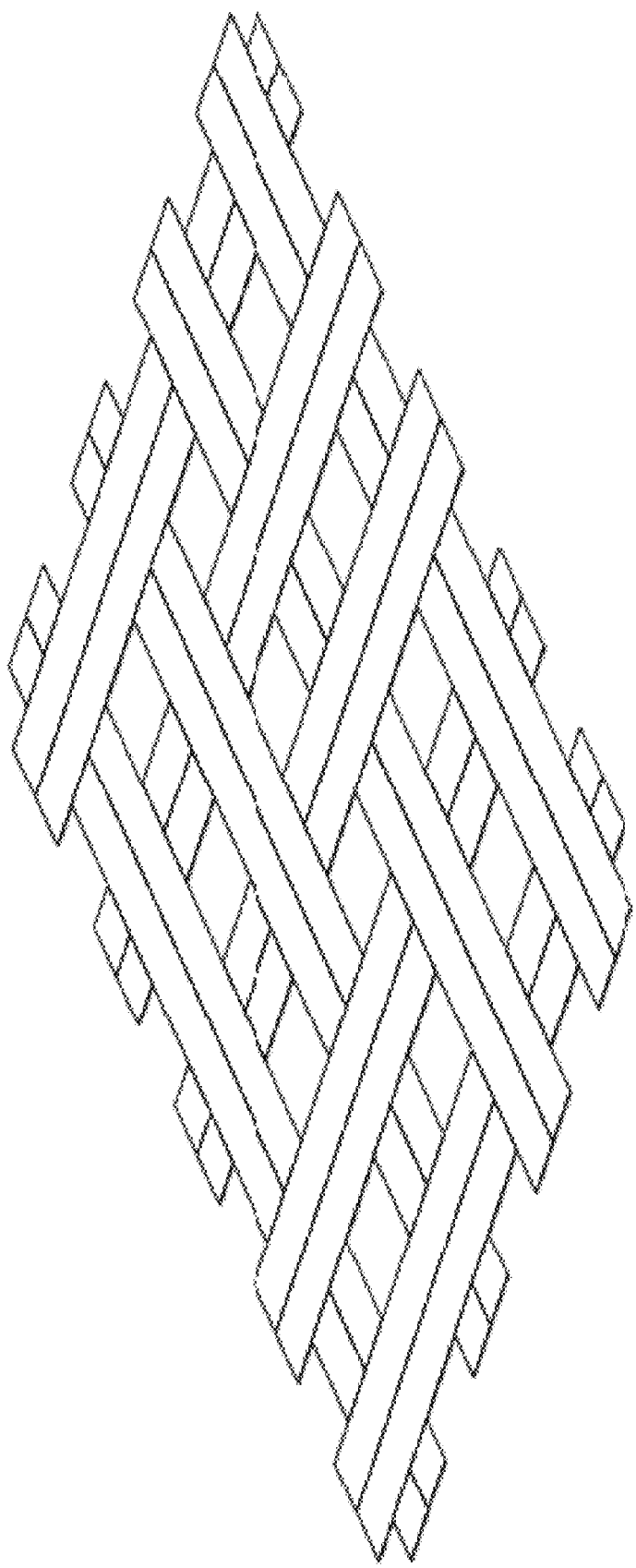
FIG. 2C illustrates a 2-dimensional rendition of a double-ended braiding pattern that may be used for the braided matrix of the hose.

The present invention provides a hose with a braided matrix and an interior lumen 10 that may be used between a PAP flow generator 05 and a sleep apnea mask 15, as in FIG. 1. The hose 10 of the present invention is capable of attenuating forces in the longitudinal and rotational directions, which is not found in prior art. Hose embodiments that are not capable of attenuating forces acting upon the hose are highly susceptible to pressure changes at the mask due to kinking or detachment of the hose, which would discontinue therapy to the user 16. The hose 10 of the present invention, however, is able to attenuate by stretching or compressing in response to forces applied to the hose 10 both longitudinally and rotationally because the hose 10 is in part comprised of monofilaments 21 in a braided matrix 20, which are illustrated in FIGS. 2A and 2B.

The braided matrix 20 is made using sets of filaments braided into a pattern 25. One possible braiding pattern 25 that may be used is shown in FIG. 2A and is given as an example that in no part limits the spirit or scope of the present invention, which is limited only by the claims. In the braiding pattern 25 of FIG. 2A, a first set of filaments 26 travels under a second set of filaments 27 and over a third set of filaments 28. These sets of filaments 26, 27, 28 all travel rotationally and longitudinally about the braided hose 10, and in FIG. 2B, where the braiding pattern 25 is shown on the hose 10, it is apparent that the first set of filaments 26 travels in a direction of rotation 26A opposite to the direction 27A that the second set of filaments 27 travels. Each set of monofilaments 21 may be comprised of one or more monofilaments 21. That is, the braid pattern 25 can be single-ended, comprised of a single monofilament 21, double-ended, comprised of two monofilaments 21 (see FIG. 2C), or up to any manufacturable quantity of monofilaments 21. One of ordinary skill in the art may substitute the braiding pattern 25 without departing from the spirit and scope of this invention.

Figure 3:
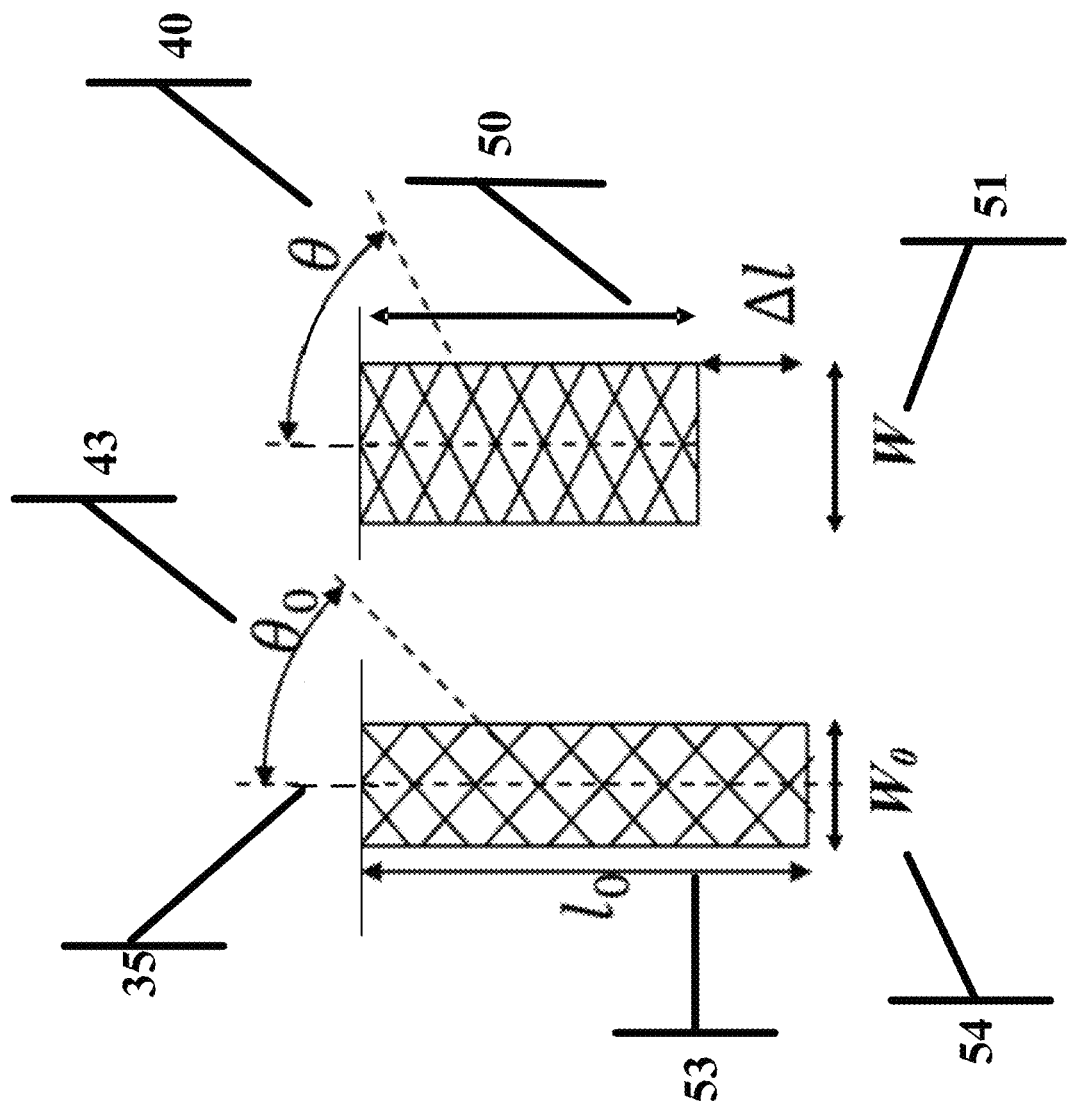
FIG. 3 demonstrates the braid angle changing in accordance with the length of the braided matrix.

The braided matrix 20 may be compressed or pulled. When there is a force in the longitudinal direction, the configuration of the braided matrix 20 would change such that the braid angle, which is defined as the angle formed between the longitudinal axis 35 of the braided hose 10 and the direction of the monofilaments 21, changes along with the length and diameter of the braided matrix 20. The right side of FIG. 3 shows the braided matrix 20 in a relaxed state, with no forces acting upon it, measuring a length of l 50 and a width of W 51. The left side of FIG. 3 shows the braided matrix 20 being stretched or stressed so that it now measures a length $l_0$ 53 and width $W_0$ 54 in a stressed state. The angle formed between the longitudinal axis 35 and the direction 27A of a first set of monofilaments 27 is θ 40 in the relaxed state (right) and $θ_0$ 43 in the longitudinally stressed state (left).

In FIG. 3, the braid matrix 20 shown on the right has a braid angle near its maximum. When the braid angle is near its maximum, it means that the monofilaments 21 are arranged to be more perpendicular to the longitudinal axis 35 than the direction of the monofilaments 21 in the stressed state (left). As the braid angle increases from $θ_0$ 43 in the stressed state to θ 40 in the relaxed state, the width of the braided matrix 20 radially expands from $W_0$ 54 to W 51. A braided hose 10 with a maximized braid angle 40 in its relaxed state can only stretch or elongate but cannot compress longitudinally. A preferred embodiment can elongate to 130%-170% of the unelongated state. This arrangement of the monofilaments 21 at the maximized braid angle 40 in the relaxed state decreases the interstitial space between the monofilaments 21, which in turn increases the kink resistance and crush resistance of the braided hose 10. Functionally, that translates into a braided hose 10 that does not need a large, heavy, inflexible, and thick-walled interior lumen 30. The decrease in the interstitial space also increases the PIC (per-inch-count of the braid matrix 20) and decreases the braided matrix length 50 by ΔI, as in FIG. 3. The construction of the braided hose 10 with a maximized braid angle 40 in a preferred embodiment has 17-24 PICs. The maximum braid angle 40 can be achieved by either directly braiding the monofilaments 21 in a compressed state, or it can be achieved by braiding the monofilaments 21 in an elongated state and then compacting the braid matrix 20 at a later time.

Since a braided hose 10 with a maximum braid angle 40 in the relaxed state cannot be compressed further in any direction, in the rotational direction as well the braided hose 10 can only elongate or stretch. Because the braided matrix 20 of the hose 10 can stretch while resisting kinks in response to either a longitudinal or a rotational force, a force applied at one end of the braided hose 10 would not result in an equivalent force at the other end of the braided hose 10 while the braided hose 10 is stretching, as occurs in conventional hose or tube embodiments of the prior art. This has advantages to the user 16 because movement during sleep using the hose 10 of the present invention would be less likely to result in leaks, reduction in pressure, kinks, or disconnections of the hose that could disrupt or discontinue treatment or therapy than hose embodiments encountered in the prior art.

The air supplied by the PAP machine or flow generator 05 travels to the sleep apnea mask 15 for the user 16 in the interior lumen 30 of the braided hose 10. The cross-sectional area of the interior lumen 30 may be a round shape, a flat shape, or a combination of round and flat without departing from the spirit and scope of the invention. These possible cross-sectional areas are illustrated in FIGS. 4-6.

The force enacted upon the braided hose 10 is generated by the sleeping user changing positions, e.g. turning over from one side to another. A hose 10 at the end of its slack, which cannot stretch, will dislodge either the mask 15 or the flow generator 05 with any movement from the user. The same hose 10 that can stretch will accommodate for the movement of the user, preventing dislodgement. There will still be a resultant force placed upon the hose pulling in a direction away from the user and flow generator 05. The stretching hose creates a resultant force, F, similar to a spring, and follows Hooke's Law, F=k(X), with a constant elastic response, k, while stretching by a distance, X. A preferred embodiment has an elastic response in the range between 0.7 to 1.7 lb/in (120 to 300 n/m). If the user continues to move away from the flow generator 05, the hose 10 will continue to stretch to its maximum length.

Figure 7C:
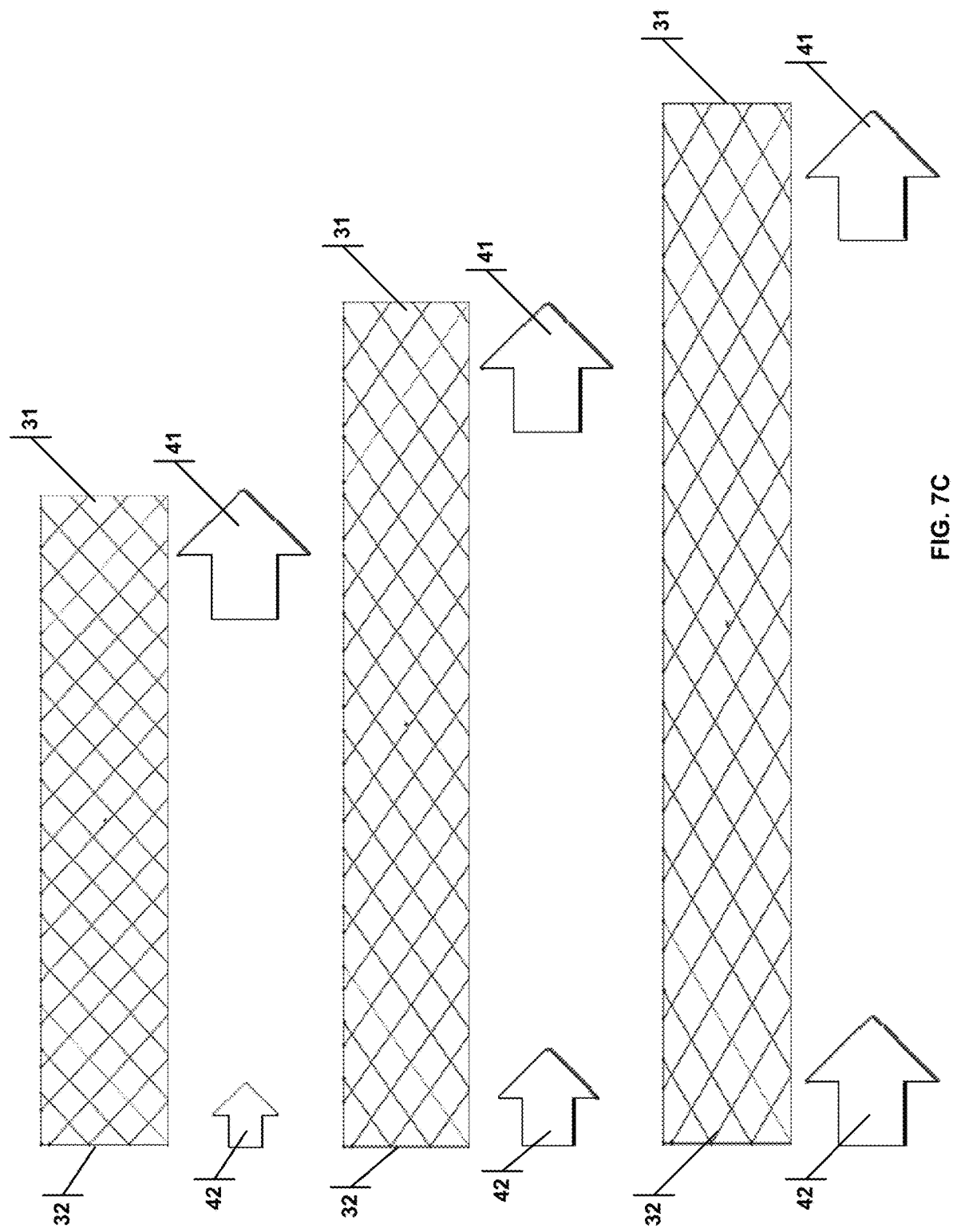
FIG. 7C illustrates a first stressed state (top), a second more-stressed state (middle) and a third most-stressed state (bottom) for the braided hose.
Figure 10:
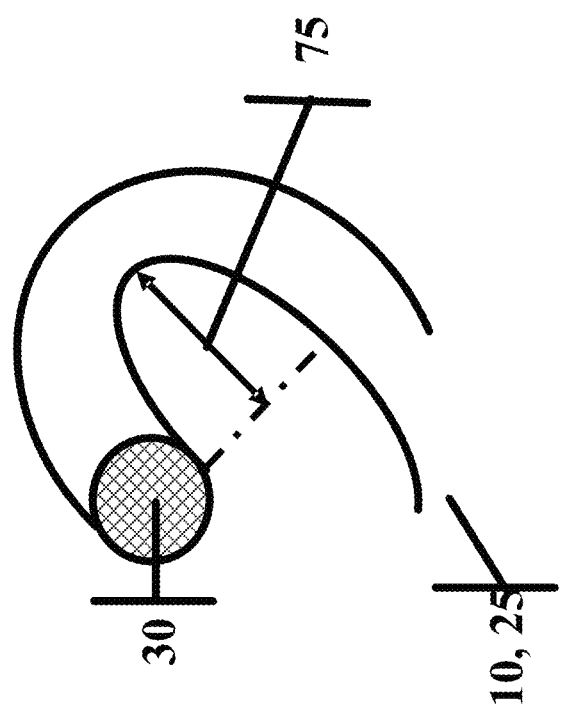
FIG. 10 illustrates the bend radius of the hose.

In FIGS. 7A and 7B, the braided hose 10 of the present invention is shown with a first end 31 and a second end 32, as well as a longitudinal axis 35 that runs along the lumen 30. The configuration of the braided matrix 20 with a maximum braid angle 40 in the relaxed state is such that when a longitudinal force 41 is introduced at a first end 31 of the braided hose 10 as shown in FIG. 7B, the force 42 experienced at the second end 32 of the braided hose 10 is not substantially a 1:1 ratio but is substantially attenuated so that the force 42 experienced at the second end 32 is substantially less than the initial force 41 exerted at the first end 31 of the braided hose 10. The difference between the force experienced from the first end 31 to the second end 32 is inversely proportional to the elongation of the braided hose 10. As the braided hose 10 elongates, the force experienced at the second end increases proportionally until it reaches its maximum, at the braided hose's 10 maximum length. In that fully extended state, the force experienced at the first end 31 is equal to the force experienced at the second end 32. This incremental increase of the experienced force as the braided hose 10 extends is shown in FIG. 7C. It should further be noted that in FIG. 7C, the longitudinal force at the second end 42 increases proportionally to the decreasing braid angle. At a certain point, the braid angle can no longer decrease, and the hose 10 operates like a rope, transferring the entire longitudinal force 41 at the first end 31 to the second end 32. This is graphically shown in FIG. 7C in the bottom hose where both the first end and second end longitudinal forces (42, 41) are shown with the same size vector arrows.

As the braided hose 10 elongates, the braid angle 40 decreases, thereby increasing the internal stress of the hose and inclining it to elastically return to a relaxed state. This effect is compounded by the addition of a polymer that will elastically deform, becoming inclined to return to its relaxed, unstressed, state. Similarly, when a rotational force 46 is introduced at the first end 31 of the braided hose 10, as in FIG. 8B, the rotational force 47 at the second end 32 of the braided hose 10 is substantially less than the first rotational force 46 because of the attenuation effect of the braid matrix 20. The attenuation of forces acting upon the braided hose 10 is independent of the direction of the force, which may act upon the hose longitudinally, laterally, rotationally, or any combination thereof. Thus, when the braided hose 10 of the present invention connects the PAP flow generator 05 to the sleep apnea mask 15, the flow generator 05 and the mask 15 are isolated from torsional forces acting upon the braided hose 10, preventing accidental disconnections, leaks, and reductions in air pressure due to kinks, which significantly improves upon prior art.

Because the braided hose 10 of the present invention has a resting state braid angle 40 substantially perpendicular to the longitudinal axis 35 of the lumen 30, when the braided hose 10 and therefore the braided matrix 20 is stretched or elongated, the braid angle decreases. FIGS. 7B and 8B respectively show that the braid angle 43 of the longitudinally stressed state and the braid angle 48 of the rotationally stressed state are less than the braid angle 40 of the relaxed state, where there are no external forces acting upon the braided hose 10. The difference in braid angles between the relaxed state and the stressed state(s) should, in a preferred embodiment, be at least 30 degrees to ensure a good extent of flexibility in the braided hose 10.

In the absence of a conventional thick polymer for the inner lumen 30 of a braided hose 10, the application of a light coating of a polymer 60 is appropriate to fill the voids of interstitial space 59 between the monofilaments 21 of the braided matrix 20 in the braided hose 10 and to coat the exterior and interior of the braided hose 10. This transforms the braided hose 10 into a pressurizable, airtight hose having a substantially smooth bore and a smooth outer surface. The application of the polymer 60 to the interstitial spaces 59 integrates the polymer 60 and the braided matrix 20 into a single uniform structure, further decreasing the propensity for the hose 10 to become entangled. The braided matrix 20 then becomes a lattice structure whose interstitial space or voids 59 are filled by the polymer 60. The cross-sectional view of the polymer 60 filling the interstitial spaces 59 of the braided matrix 20 is shown in FIG. 9.

In selecting the polymer 60 used to coat the braided matrix 20, it is essential for the material to be elastomeric and with minimal thickness, preferably less than 0.03 in (0.08 mm) thick per wall, and without nodules. By carefully selecting a polymer 60 that fulfills these requirements, the flexibility of the braided hose 10 is retained. In other words, the difference between the outer diameter 70 of the finished braided hose 10 and its inner diameter 65 should be as small as possible without detriment to the structure of the braiding in order to retain flexibility and the desired attenuation of forces. In contrast, if the polymer 60 is rigid or too thick a coating is applied, the braided hose 10 would become more stiff, rigid and inflexible, similar to a conventional polymer hose, thus losing its unique advantages. The polymer 60 also needs to be substantially airtight and adds to the structural effects of the hose 10 by increasing the kink and crush resistance as well as the elastic memory of the braided matrix 20. The increase in kink and crush resistance is caused by the polymer 60 adding more material in the interstitial space 59 in the braid pattern 25, which must be displaced when acted upon by a force perpendicular to the longitudinal axis 35. This perpendicular force can be a directly applied force, such as the by an appendage of the user, or indirectly by the longitudinal extension of the braided hose 10 in a coiled position. The construction of the braided hose design interlaced with a polymer makes occlusion impossible from purely longitudinal forces. As the hose extends, the diameter will decrease as the braid angle becomes more longitudinal; at a certain point the material of the monofilaments with the interstitial polymer would resist any further constriction of the braided hose 10. The increase in elastic memory is caused by curing the polymer 60 to a specific orientation, to which it will return after it has been deformed.

Only specific types of polymers 60 are appropriate, as the polymer 60 must be viscous enough to enter between the interstitial spaces 59 of the braided matrix 20 and be applied thinly enough so as to not stiffen the braided hose 10 into a polymer tube. A preferred polymer is a silicone dispersion because it does not support microbial growth, has a low chemical reactivity and toxicity, and is stable and inert. Additionally, silicone dispersion can be applied on the inside and outside of the interstitial voids 59 of the braided matrix 20 with a thin coating and does not delaminate from the braided matrix 20 when abraded. Also, when the silicone is utilized in the quantity and method described herein, it does not have an undesirable surface finish (e.g. sticky or tacky) for skin contact when the user 16 touches the hose 10.

If all the previous requirements in braiding the monofilaments 21, setting the maximum braid angle 40, and selecting an appropriate polymer 60 are fulfilled, the braided hose 10 should be able to bend flexibly, with a small bend radius 75 without kinking the hose 10 or affecting the pressure of air in the interior lumen 30. In a preferred embodiment, the braided hose 10 can support a bend radius 75 of 0.7 in without resulting in kinks that affect the flow or pressure inside the interior lumen 30, shown in FIG. 10.

Figure 11:
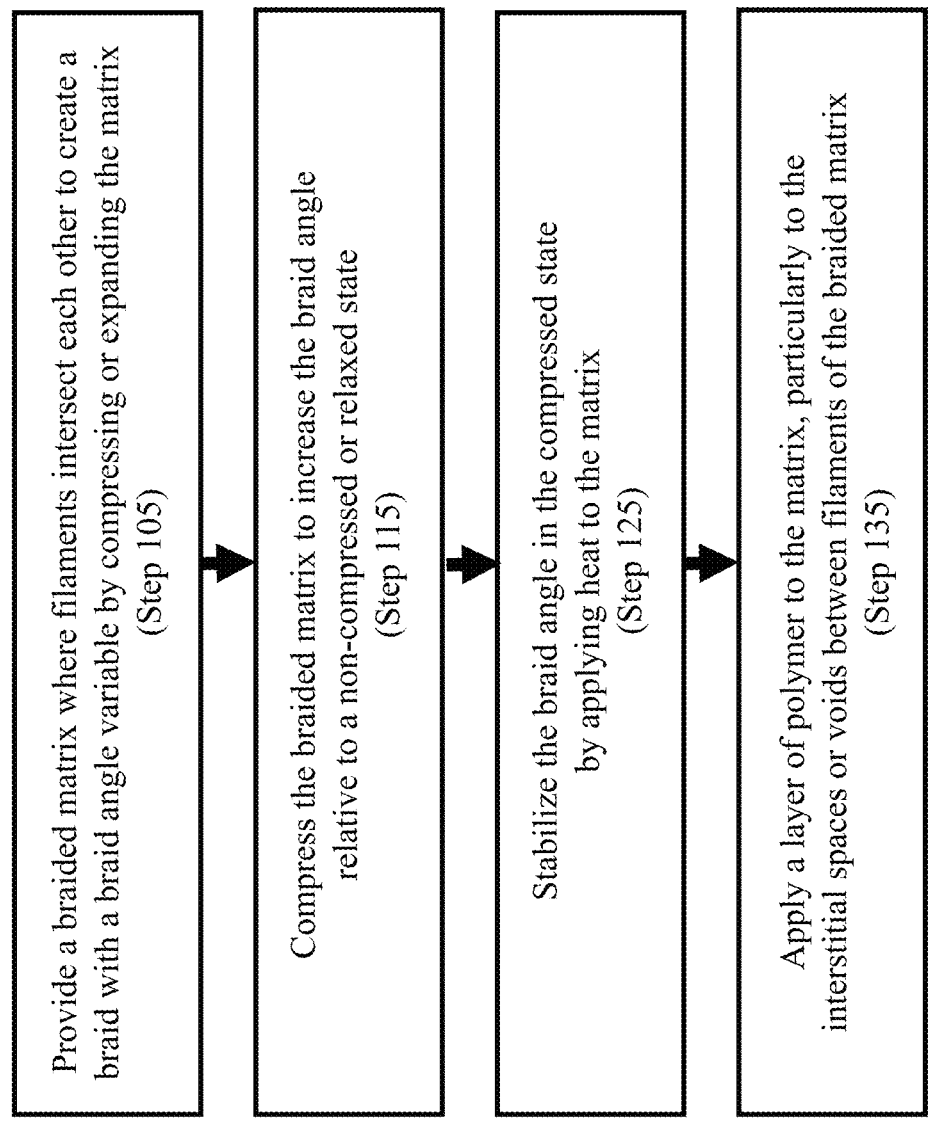
FIG. 11 presents the steps of relevance to manufacturing the braided hose of the present invention.

FIG. 11 illustrates the major steps needed to manufacture the braided hose 10 that is disclosed by the present invention. The method 100 of manufacturing the braided hose 10 as taught by the present invention consists of steps 105-135. First, a braided matrix 20 with an interior lumen 30 should be provided in step 105; materials for the filaments used to form the braided matrix may be selected from nylon, PET, PEN, PP, and/or PEEK.

Next, the braided matrix 20 should be compressed in step 115, such that the braided matrix 20 has a maximum braid angle 40. In step 115, the braided matrix 20 is preferably compressed at least 50% lengthwise compared to a non-compressed or relaxed state, and the braid angle 40 of the compressed matrix is preferably increased by at least 30 degrees in step 115.

After compressing the braided matrix 20 in step 115, the braid angle 40 should be stabilized in step 125, which may be achieved through heat setting the braid. After step 125, the braided matrix 20 elastically returns to the relaxed state with a maximum braid angle 40 after being deformed by elongation or torsion. This stabilization step essentially flips the matrix's relaxed and stressed states—prior to stabilization, the matrix's relaxed state has a braid angle that is less than the stressed state, while after stabilization the opposite is true.

Finally, a polymer 60 may be applied to the braided matrix 20 in step 135, in the interstitial spaces 59, interior, and exterior of the braided matrix 20, preferably with a polymer coating thickness of less than 0.03 in. As discussed previously, a preferred polymer 60 is a silicone dispersion. Compared to the length of the braided matrix 20 after stabilization (step 125), the braided matrix 20 should preferably be capable of stretching 130% of the post-stabilization length after the polymer 60 has been applied (step 135).

In step 135, the polymer 60 may be applied to the interior surface of the braided matrix 20, the outer surface of the braided matrix 20 or some combination thereof; however, it is preferred that the braided matrix 20 be coated with the polymer 60 on both the inner and outer surface, so that the inner lumen 30 of the braided hose 10 has a substantially smooth bore in order to minimize airflow resistance. More specific information related to manufacturing the braided hose 10 follows.

In the manufacture of the braided matrix 20, the stabilization of the braided hose 10 through the application of heat can create an equilibrium point for the braid angle 40; this process is also known as heat setting the braid. The changes of the braid properties between a heat stabilized braided hose is shown in Table 1, produced below.

TABLE 1

Properties of Unprocessed vs Heat stabilized Braided Hose

| Characteristic | Unprocessed Properties of a Braided Tube | Properties of Polymer Dipped, Heat Stabilized Braided Hose |
|---|---|---|
| Braid Angle | 30° | 60° |
| Pic Count | 12-19 Pics per in. | 17-24 Pics per in. |
| Length | 100% | 50% |
|  | Nominal: 12.0 ft (3.6 m) | Nominal: 6.0 ft (1.8 m) |
|  | Range: 10.0 to 14.0 ft (3.0-4.3 m) | Range: 5.0 to 7.0 ft (1.2-2.1 m) |
| Outer Diameter | N/A (Braid is substantially flattened around a spool) | Nominal: 0.37 in (9.4 mm) Range: 0.30 to 0.50 in (7.5-12.5 mm) |
| Inner Diameter | N/A (Braid is substantially flattened around a spool) | Nominal: 0.32 in (8.1 mm) Range: 0.25 to 0.40 in (6.4-10.1 mm) |

Heat setting ensures that the braid angle 40 along the length of the braided hose 10 stays near its maximum when no forces are exerted upon the braided hose 10. Heat setting guarantees that when deformation (i.e. stretching and/or twisting) occurs, the braided hose 10 will elastically return to its relaxed state, where the braided angle 40 is maximized. Additionally, heat setting the braided matrix 20 allows it to be further processed more easily. Heat setting requires the use of a monofilament 21 that will plastically deform with the application of heat, such as a thermoplastic or memory metal. This process should be done when the braided matrix 20 is covering an internal core to ensure that the braid does not set anywhere along its length in a necked down position. The inner core may be slightly smaller, by approximately 0.005-0.015 in (0.127-0.381 mm), compared to the maximum size of the braid, in order to ensure that the braid matrix 20 stays near its maximum braid angle 40. The fit between the inner core and the braided hose 10 should be loose enough that the braided hose 10 can be ejected off of the internal core after heat setting. The inner core can be made from individual mandrels or a stationary core.

Figure 12:
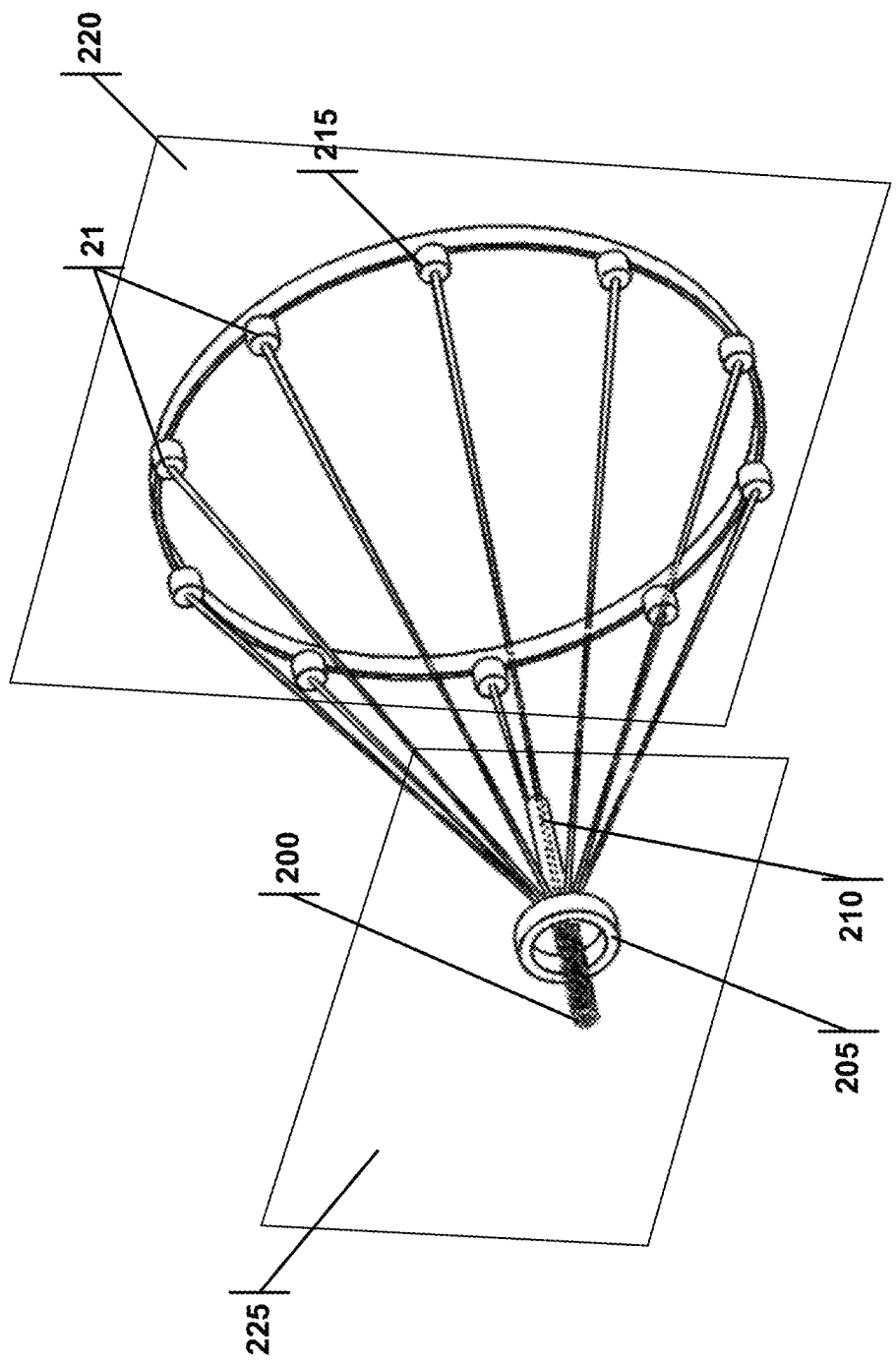
FIG. 12 illustrates an apparatus for manufacturing and heat setting the braided hose using a stationary mandrel.

FIG. 12 illustrates an apparatus for manufacturing and heat setting the braided matrix. A spool track with monofilament carriers 215 rotates within a spool plane 220 and releases monofilaments 21 that converge and interweave at the convergence zone 225 about a stationary mandrel 210. This interweaving creates a braided matrix 200. Near to the convergence zone 225, a ring heater 205 must be placed to heat the braided matrix 200 to the setting temperature while it is simultaneously being pulled off the stationary mandrel 210. The previously specified component locations are requisite to have a core on which to set the braided matrix 200 to the correct diameter, but should not be distanced long enough that the braided matrix 200 would become stuck and neck down so that it cannot be removed with a tensile load. The braided tube, set to the correct diameter, can then be wrapped around a spool for shipment, storage or usage, and the requisite length can then be cut at a later time.

Figure 13:
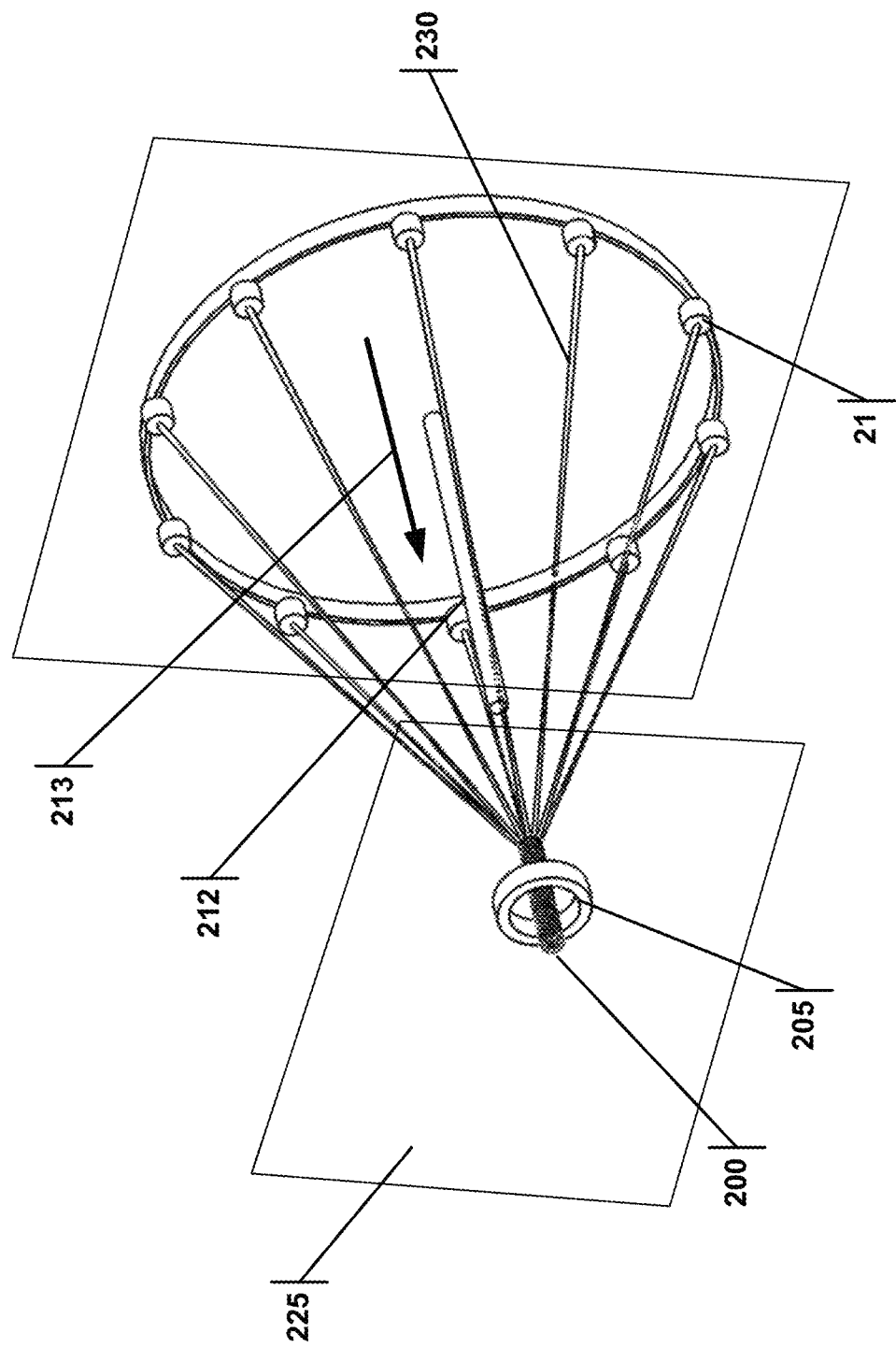
FIG. 13 illustrates an apparatus for manufacturing and heat setting the braided hose using a mobile mandrel.

An alternative method for manufacturing utilizes a mobile mandrel, instead of a stationary one onto which the matrix is braided, is shown in FIG. 13. A mobile mandrel 212 is loaded behind the convergence zone 225 into the braided matrix 200. The mobile mandrel 212 will move in the direction 213 of braiding until the mandrel 212 is fully enveloped by the braided matrix 200. The braid covered mandrel can then be heated through a single or series of heater rings (as in FIG. 12) through which it can pass. The braided matrix 200 can alternatively be cut after the end of the mobile mandrel 212, creating a mobile braid-covered mandrel, which can be removed. Once removed, the braid-covered mandrel can be heated alone or in a batch in an oven to set the braid to the diameter of the mandrel. At that point, the mobile mandrel 212 can be delaminated to remove the braided matrix from the mandrel.

It is preferable to have an inner core with a high thermal conductivity, such as stainless steel, so as to heat the braided hose 10 evenly from all sides. The application of heat must be below the melting point and preferably above the glass transition temperature, so as to allow the material to deform plastically but not degrade. The preferred heat setting temperature with PET material is 220° C. (428° F.), which is between the melting point of 250° C. (482° F.) and the glass transition temperature of 67° C. (153° F.). As the heating temperature increases, the time it takes to set the braid inversely decreases. The preferred time to heat set is between 0.5 min and 1.5 min.

The braided hose 10 is preferably heat set to a length at least as long as the length of the desired finished tube, e.g. preferably 6 ft (183 cm), to create a continuous length of braided hose 10. Longer braided hoses may be heat set in increments of the preferred length of the braided hose 10. The heat setting of the braid can be done at the time of braiding of the monofilaments 21 onto a mandrel, as an in-line process, or can be done separately, such as when the braided matrix 20 is loaded onto a mandrel after braiding.

The performance characteristics of the braided hose 10 greatly depend upon the following factors: a) the braid pattern 25, b) the diameters of the braided tube 10 and the size of the monofilaments 21, and c) the material of the braided matrix 20.

The braided pattern 25 affects the kink resistance, crush resistance, expansion/compression ratio and stiffness of the braided matrix 20. The braid pattern 25 is preferably run double-ended, at a full load, where a first pair of monofilaments 26 travels under a second pair of monofilaments 27 and then travels over a third pair of monofilaments 28 while the first and second pairs of monofilaments 26 and 27 are rotating in opposite directions 26A and 27A. This braid pattern 25 utilizes a 100% carrier capacity of the braiding machine, meaning that this braid pattern has the most proficient linear throughput.

The size of the braided hose 10, as measured by either its inner diameter 65 or by its outer diameter 70, and/or by the size of the monofilaments 21, affects the braid's aspect ratio, which in turn dictates the performance of the braided tube 10. A large diameter braided tube 10 with small monofilaments 21 will have a very different performance than a small diameter braided tube 50 with large monofilaments 21. A preferred embodiment can be constructed with a wall thickness to cross-sectional area ratio of less than 0.5 in/in$^2$ and preferably greater than 0.2 in/in$^2$. A preferred embodiment has an outer diameter 70 ranging from 0.30 to 0.50 in (7.5-12.5 mm) with a monofilament 21 diameter of 0.005-

0.015 in (0.127-0.381 mm). Both round and flat fibers of different sizes can be used, but a round fiber is preferred due to its uniform characteristics when manipulated in different orientations.

The material of the braid matrix 20 additionally affects the performance of the finished braided hose 10. Memory metal, plastic wires/fibers, Stainless Steel, Copper, NiTi, Titanium, Platinum, Cobalt Chromium/Nylon, PET, PEN, PP, and/or PEEK, can be used as the filaments for the braid, but a polymer material, specifically a polyethylene terephthalate (PET) monofilament, is preferred. PET material is well suited for this application because it is semi-rigid, very lightweight, forms a good gas and moisture barrier, is impact-resistant and has a good tensile strength.

Provided below are the properties of a preferred embodiment of the braid matrix 20 and finished braided hose 10, hereinafter "the FRESCA hose". The superior performance of the FRESCA hose is its performance is due in part to the ratio of wall thickness to cross-sectional area. While the specifications of a hose are affected by material, design, size, and structure, the wall thickness to cross-sectional area is a good performance indicator of the hose. Having a lower wall thickness to cross-sectional area ratio allows for a more lightweight and flexible hose while maintaining a large cross-sectional area for high flow rates. The FRESCA hose is able to achieve a low wall thickness to cross-sectional area ratio of only 0.26.

TABLE 2

Braid/Hose Properties of the Preferred Embodiment
BRAID/HOSE PROPERTIES

| | |
|---|---|
| Monofilament Diameter | Nominal: 0.01 in (0.25 mm) |
| | Range: 0.005 to 0.015 in |
| | (0.127-0.381 mm) |
| Material | PET |
| Shape | Round |
| Color | Black |
| Carriers | 32 Carriers |
| Pattern | Regular |
| | (Full load = 1 over 2 under 2) |
| Configuration | Double Ended |
| Pick Count | 19-22 Pics per in. |
| Wall Thickness | Nominal: 0.025 in (0.64 mm) |
| | Range: 0.02 to 0.03 in |
| | (0.50-0.76 mm) |
| Polymer Coating | NuSil MED 16-6606 Silicone Dispersion |

The braided matrix may also include shielded or insulated metal wires, open lumens, or heatable elements woven into the braided matrix. This is shown in FIG. 13, with shielded or insulated metal wires, open lumens, or heatable elements 230 being woven together with the monofilaments 21. These wires or lumens can be in addition to the monofilaments in the braid pattern, or in substitution for one or more of the monofilaments. The utility of these wires or lumens is to connect an electrical or pneumatic sensor or other device located in the headgear, mask or on the hose, to the flow generator. The heatable elements may be used to heat the length of the hose to prevent condensation, also known as rain out, from occurring within the hose or mask or as a comfort feature.

The FRESCA hose 10 has a low weight/length ratio, which is less cumbersome and more convenient for the user 16, due to the aforementioned properties (see Table 2). In addition, the small bend radius 75 and high droop percentage indicate a high flexibility of the braided hose 10, which allows for an increased range of motion for the user 16. Lastly, the hose 10 has the ability to readily stretch with tensile loads. This is a useful feature for decoupling tensile loads due to force on the hose 10. Additionally, while stretching the hose 10 affects flow rates, the pressure of air flow within the hose is unaffected even at +10% or +20% stretched lengths. Maintaining pressure while stretching the hose 10 means fewer impediments with PAP therapy in situations where the user 16 stretches the hose 10.

To clarify further, traditional PAP systems utilize a mask 15 with an intended leak. Pressure is created by excess air flow creating a back pressure against the intended leak. Small variations in air flow directly affect the pressure developed in the mask 15. Therefore, traditional PAP masks are highly reliant on receiving a particular amount of airflow to achieve pressure.

The FRESCA system uses an expiratory valve that governs exhalation resistance. Therefore, it is not as susceptible to changes in air flow. If enough flow is being delivered to counteract any non-intended leak from the mask, the FRESCA system will become pressurized. Because of this, the FRESCA system can tolerate a hose 10 that stretches and consequentially reduces the airflow delivered to the user as seen in Table 3 and Table 4. Table 3 shows the reduction in airflow from elongating the hose an additional 10 & 20% at pressures of 4, 12, & 20 cm $H_2O$. Table 4 shows the negligible effect from the reduction of flow caused by the elongation of the hose at pressures of 4, 12 & 20 cm $H_2O$.

TABLE 3

FRESCA System Stretch vs. Flow Rate

| Stretch percent | PAP Pressure | Initial Flow Rate (L/Min) | Stretched Flow Rate (L/Min) | Percent Change |
|---|---|---|---|---|
| 10% | 4 | 17.6 | 15.1 | −14.0% |
| | 12 | 30.1 | 25.4 | −16% |
| | 20 | 39.0 | 32.2 | −17% |
| 20% | 4 | 17.6 | 12.3 | −30% |
| | 12 | 30.1 | 21.6 | −28% |
| | 20 | 39.0 | 27.5 | −30% |

TABLE 4

FRESCA System Stretch vs. Pressure

| Stretch percent | PAP Pressure | Initial Measured Pressure (Cm-H2O) | Stretched Measured Pressure (Cm-H2O) | Percent Change |
|---|---|---|---|---|
| 10% | 4 | 3.8 | 3.8 | 0% |
| | 12 | 11.8 | 11.8 | 0% |
| | 20 | 19.8 | 19.8 | 0% |
| 20% | 4 | 3.8 | 3.8 | 0% |
| | 12 | 11.8 | 11.8 | 0% |
| | 20 | 19.8 | 19.8 | 0% |

While in some applications braided hoses are common, previously disclosed and available hoses are used for a very different purpose and are constructed in a significantly different manner, such that they are not well-suited for use in sleep apnea systems. Braided hoses are mainly used in high pressure applications, greater than 7000 cm $H_2O$ (100 psi), where the braid can be used to reinforce an underlying airtight polymer hose. The unique braided hose structure and method of construction described herein may be applicable to other applications outside the scope of PAP therapy. Other medical respiratory, pneumatic, or general fluid line applications may find the unique characteristics of this hose appropriate to their intended use.

PAP therapy is working within pressures in the 2-30 cm H₂O (0.03-0.43 psi) range, several orders of magnitude less than typical reinforced braided hoses. Reinforced braided hoses have braid covering the outer surface of a polymer tube or layered between two different polymer tubes, co-extruded in the wall of the polymer or otherwise constructed. This construction utilizes the polymer hose as an airtight conduit for the delivery of a pressurized medium and the braid to act solely as reinforcement to the underlying hose. The reinforcement from the braid only works in this construction as a protection from over-expansion due to internal hoop stresses. As the tube fills with pressure, it expands against the braid, which constrains it to the size of the braided frame. Typical reinforced braided tubes require a large polymer wall thickness to provide adequate kink and crush resistance, reducing flexibility and suitability for use in PAP system applications.

Due to the polymer thickness of traditional braided hoses, they are often large, heavy, inflexible and unable to attenuate forces—thus not well-suited as a hose for the delivery of PAP therapy. For comparison, provided below is the analysis of two types of common braided hoses—integrated braided hoses and externally braided hoses.

For a braided hose with an integrated braid, the sample used for comparison was a high-pressure PVC tubing with an inner diameter of 0.25" and an outer diameter of 0.50". In this conventional construction, the wall thickness to cross-sectional area ratio is 2.54. Compared to the FRESCA hose's ratio of 0.26, this represents nearly a ten-fold difference. Table 5 below presents the performance characteristics of the PVC hose. The PVC hose is relatively heavy, not particularly flexible, has poor stretch, and is not intended to provide a supple feel. These characteristics make the hose less than ideal for PAP users who require both comfort and functionality.

TABLE 5

Performance Characteristics of the Integrated Braided PVC Hose found in Prior Art

| Characteristic | Value |
|---|---|
| Wall thickness/cross sectional area ratio | 2.54 |
| Weight/Length ratio | 1.28 oz/ft |
| Bend Radius | ~0.7" without kinking |
| Droop percent | ~36% droop distance over a 1 ft length |
| Stretch | ~0% (1 ft section loaded with 500 gm) |
| Crush distance/inner diameter percentage | ~23% of ID crushed for 5.5 lbf applied over a 2 in length |

Another example from the prior art is a high-pressure hose with an external braid cladding over an internal tube. The sample used for comparison had an inner diameter of 0.20" and an outer diameter of 0.30". Its wall thickness to cross sectional area ratio is 1.59—compared to the FRESCA hose's ratio of 0.26, this is nearly a 6-fold difference. Table 6 below lists the performance characteristics of the externally braided hose. Again, the externally braided hose is relatively heavy, not particularly flexible, has poor stretch, and is not intended to provide a supple feel. The poor characteristics of other types of braided hoses contrast sharply with the novel properties of the FRESCA hose.

TABLE 6

Performance Characteristics of the Externally Braided Hose found in Prior Art

| Characteristic | Value |
|---|---|
| Wall thickness/cross-sectional area ratio | 1.59 |
| Weight/Length ratio | 0.32 oz/ft |
| Bend Radius | ~0.7" without kinking |
| Droop percent | ~71% droop distance over a 1 ft length |
| Stretch | ~7% (1 ft section loaded with 500 gm) |
| Crush distance/inner diameter percentage | ~35% of ID crushed for 5.5 lbf applied over a 2 in length |

The superior performance of the FRESCA hose has multiple benefits for a PAP user. A typical PAP user attempts to sleep while wearing a mask for PAP treatment. Due to the sleep apnea condition, PAP patients intrinsically have issues with obtaining proper sleep. Any additional external distractions further prevent the user from obtaining proper sleep. To that end, user perception, user interaction, and user comfort are just as important as the functional performance of the FRESCA hose.

The FRESCA hose mitigates distractions in size, weight, flexibility, and tug as compared to a conventional PAP hose. First, the small size of the FRESCA hose is much less of a distraction for the user. The FRESCA hose diameter is approximately a third of the diameter of a typical PAP hose, reducing its visual and physical presence. A conventional PAP hose is typically uncomfortable to sleep on due to its large size. If a user lies on the FRESCA hose, however, they may not even notice that it is there, due to the relatively small size of the FRESCA hose. Moreover, for convenience during travel and storage, a user with a FRESCA hose would not need as much space as compared to using a conventional PAP hose.

Second, the weight of the hose can affect comfort during sleeping. The FRESCA hose, including a 6 ft hose, the flow generator connector, and the mask connector, weighs only 1.3 oz, whereas a conventional 6 ft PAP hose has a weight of 4.3 oz, nearly three times heavier. A lighter hose inherently creates less pull on the mask and on the flow generator. The FRESCA hose is less cumbersome compared to a conventional PAP hose and is more convenient for the user.

Third, the flexibility of the hose affects its range of motion. The FRESCA hose has a bend radius of 0.7" compared with a conventional hose that has a bend radius of ~1". The greater flexibility allows for an increased range of motion for the user. For example, users that move in their sleep can find it distracting when a typical PAP hose does not conform to the user's motion. The FRESCA hose has greater flexibility, which allows for more movement of the hose, conforming better to the user's movement.

Finally, when the hose tugs on the mask or flow generator, it can be distracting to the user during sleep. The FRESCA hose can elongate by 50% percent at a small loading of 1.1 lbs. while still providing 90% of its pressure. In comparison, a conventional PAP hose will minimally stretch. Having a high elongation is useful in that the hose decouples tensile loads from the mask and flow generator. For example, conventional PAP hoses provide nearly a 1:1 force transmission from the hose to flow generator or mask due to their poor elongation. This makes conventional PAP hoses prone to dislodging the mask or applying a distracting tug or drag to a user intent on sleeping. In contrast, the FRESCA hose will stretch, mitigating a distracting tug or drag on the user.

While CPAP is sometimes used in this disclosure, it would be apparent to those of skill in the art that the devices, methods and structures disclosed in this application may be used in systems that do not require or use constant positive airway pressure. Thus, the teachings herein are not limited to CPAP but apply equally to PAP (Positive Airway Pressure) systems and treatments for sleep apnea.

The invention has been described in connection with specific embodiments that illustrate examples of the invention but do not limit its scope. Unless indicated otherwise, any feature, aspect or element of any of these example embodiments may be removed from, added to, combined with or modified by any other feature, aspect or element. As will be apparent to persons skilled in the art, modifications and adaptations to the above-described example embodiments of the invention can be made without departing from the spirit and scope of the invention, which is defined only by the following claims.

The invention claimed is:

1. A method of manufacture of a hose, the method comprising:
   providing a braided matrix with an interior lumen, the matrix including:
      filaments that intersect each other and create a braid;
      a longitudinal axis that runs along the lumen, wherein the filaments intersect the longitudinal axis at a braid angle;
      and wherein the braid angle can be varied by compressing the matrix along the direction of the longitudinal axis or by expanding the matrix perpendicular to the longitudinal axis;
   compressing the matrix so as to increase the braid angle relative to the braid angle of the matrix in the non-compressed state;
   stabilizing the braid angle by applying heat to the matrix; and
   applying a polymer to the matrix.

2. The method of claim 1, wherein the matrix is compressed at least 50% prior to the stabilization step.

3. The method of claim 1, wherein the braid angle is increased by at least 30 degrees prior to the stabilization step.

4. The method of claim 1, wherein after the polymer is applied, the hose is stretched.

5. The method of claim 1, wherein the matrix has a length after the stabilization step and the method further includes stretching the matrix by at least 130% of the length after the polymer is applied.

* * * * *